United States Patent [19]

Elings

[11] Patent Number: 4,608,990

[45] Date of Patent: Sep. 2, 1986

[54] MEASURING SKIN PERFUSION

[76] Inventor: Virgil B. Elings, P.O. Box 6463, Santa Barbara, Calif. 93111

[21] Appl. No.: 531,270

[22] Filed: Sep. 12, 1983

[51] Int. Cl.[4] .................................................. A61B 5/02
[52] U.S. Cl. .................................... 128/633; 128/666; 128/691
[58] Field of Search ................. 128/666, 633, 654, 691

[56] References Cited

U.S. PATENT DOCUMENTS

| | | | |
|---|---|---|---|
| 3,313,290 | 4/1967 | Chance et al. ...................... | 128/633 |
| 3,647,299 | 3/1972 | Lavallee .............................. | 128/633 |
| 3,677,648 | 7/1972 | Dorsch ................................ | 128/666 |
| 3,709,612 | 1/1973 | Clemens ............................. | 128/633 |
| 3,796,213 | 3/1974 | Stephens ............................ | 128/666 |
| 3,993,047 | 11/1976 | Peek ................................... | 128/666 |
| 4,109,643 | 8/1978 | Bond et al. .......................... | 128/666 |
| 4,178,917 | 12/1979 | Shapiro .............................. | 128/665 |
| 4,241,738 | 12/1980 | Lübbers et al. ..................... | 128/666 |
| 4,259,963 | 4/1981 | Huch ................................... | 128/666 |
| 4,341,223 | 7/1982 | Lutz .................................... | 128/666 |
| 4,446,871 | 5/1984 | Imura ................................. | 128/666 |
| 4,476,875 | 10/1984 | Nilsson et al. ...................... | 128/691 |

FOREIGN PATENT DOCUMENTS

| | | | |
|---|---|---|---|
| 2531854 | 2/1984 | France ................................ | 128/666 |
| 1426319 | 2/1976 | United Kingdom ................ | 128/666 |
| 2039364 | 8/1980 | United Kingdom ................ | 128/666 |

OTHER PUBLICATIONS

Jacobs et al., "Determination of the Accuracies of Dye-Dilution and Electromagnetic Flowmeter Methods of Measuring Blood Flow" *J. of Thoracic and Cardiovascular Surgery*, v.58, No. 4, Oct. 1969, pp. 601–607.

*Primary Examiner*—John Doll
*Assistant Examiner*—Lance Johnson
*Attorney, Agent, or Firm*—Charles H. Schwartz; Ellsworth R. Roston

[57] ABSTRACT

A fluorometer and method of fluorometry for illuminating an area containing fluorescent material which material fluoresces when excited with light energy at first particular frequencies and for collecting and measuring fluorescent light energy at second particular frequencies produced at the area, including, a light source for producing light energy including light energy at the first particular frequencies and with the light source having a wattage rating of no more than twenty (20) watts, pulsing the light energy at a frequency of approximately at least 10 Hz, filtering the pulsing light energy from the light source to pass substantially only the light energy at the first particular frequencies, directing the filtered pulsing light energy to the area containing fluorescent material, collecting light energy including fluorescent light energy at the second particular frequencies produced at the area and directing the collected light energy away from the area, filtering the collected light energy to pass substantially only the collected light energy at the second particular frequencies, detecting the filtered collected light energy for producing a first signal in accordance with the filtered collected light energy, and phase detecting the first signal for producing a second signal in accordance with the first signal and representative of the filtered collected light energy in phase with the filtered pulsing light energy which second signal is representative of the fluorescent light energy at the second particular frequencies produced at the area.

2 Claims, 8 Drawing Figures

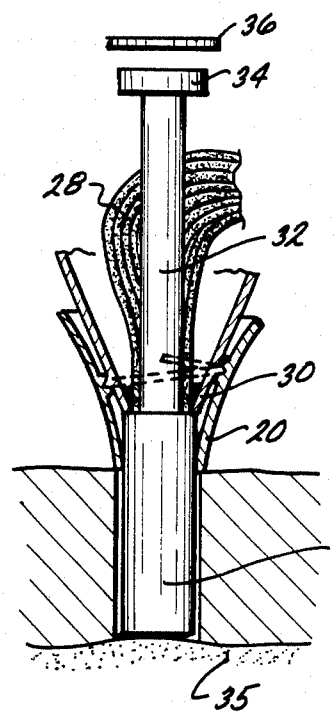
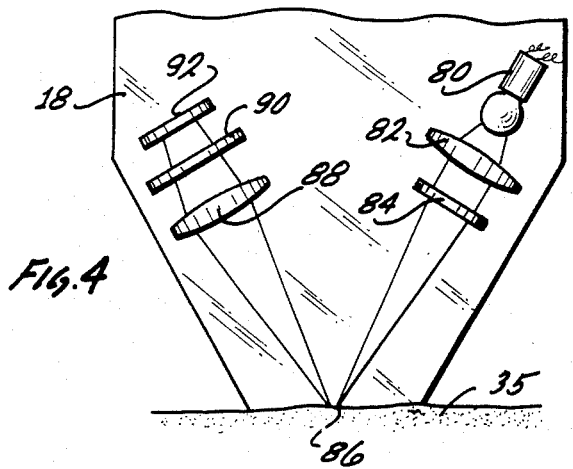
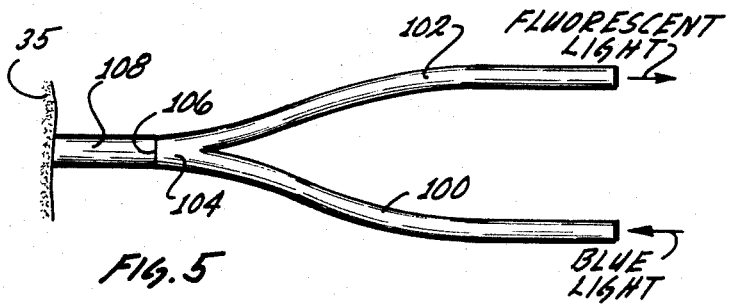
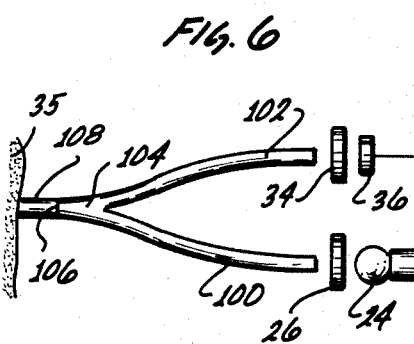
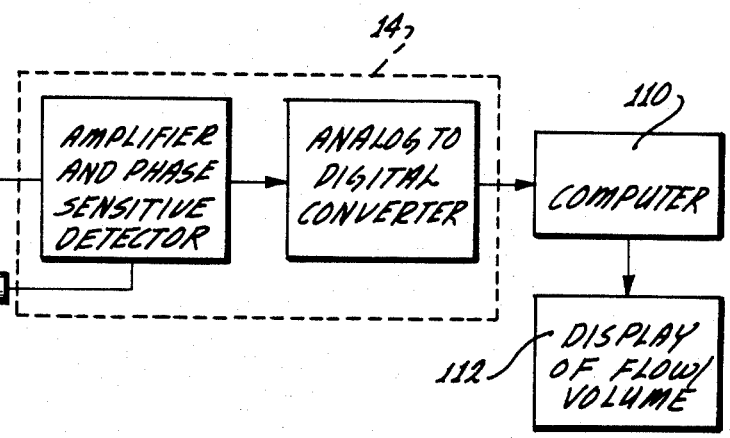
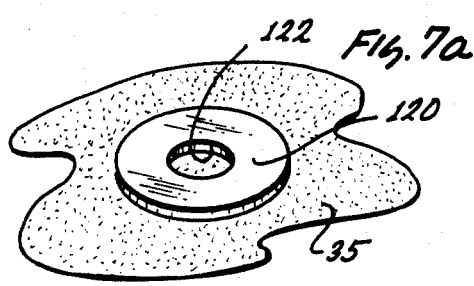
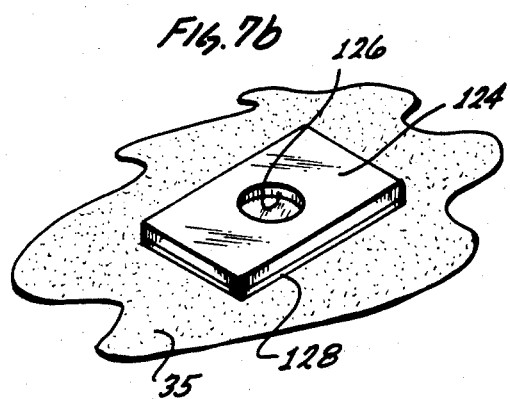

MEASURING SKIN PERFUSION

BACKGROUND OF THE INVENTION

1. Field of the Invention

The present invention relates to a skin fluorometer perfusion monitor and more specifically to a hand held skin fluorometer to measure blood perfusion at a position exterior to the skin tissue.

2. Description of the Prior Art

It is often desirable to provide for a measurement of the perfusion of body tissue by the blood. Such a measurement is useful, for example, to determine if a portion of the body is receiving an adequate supply of blood such as after a surgical procedure. For example, it would be desirable to monitor the perfusion in a body extremity, such as a finger or hand, which was either partially or completely severed and then reattached. The measurement of blood perfusion is important so as to determine the likelihood of the reattached member receiving an adequate blood supply to insure a healthy healing of the reattached member. Another area in which the monitoring of the perfusion of blood is useful is when skin flaps have been attached such as for burn victims.

One method of measuring the blood perfusion is to measure the level of fluorescense of a fluorescent dye, such as fluorescein, which is carried by the bloodstream and diffuses into particular body tissue through the blood perfusion into the tissue. The fluorescent dye may be injected into the bloodstream and with the level of fluorescense at some later time measured at the particular tissue area. The crudest way of injecting the dye into the bloodstream is to ingest the dye but this takes a considerable time before the dye ultimately get into the blood.

A more common method is to inject the dye directly into the bloodstream and then wait for about fifteen (15) minutes for the dye to diffuse into the tissue of interest. A measurement of the fluorescense of the tissue of interest, such as a reattached finger, is then made and with a comparison made between the fluorescence at the reattached finger and at a normal finger. It would be useful to make this measurement on a regular periodic basis, such as every hour, so that if a blockage of either the artery or vein to the reattached area occurs, the blockage can be detected within a short time and surgery can be performed to cure the blockage before the reattached area dies because of a lack of blood supply.

The general methods of measuring this perfusion into the blood tissue, using fluorescense, has been of two (2) types. First, the intensity of the fluorescense may be measured directly with the eyes but such a qualitative measurement requires large doses of fluorescent dye and such large doses cannot be repeated on a periodic regular basis such as every hour.

Another method of measuring uses a fluorometer which has a long optical fiber bundle and with this bundle carrying blue exciting light to the skin through a first group of fibers in the bundle and with a detection of the fluorescense with the remaining group of fibers in the bundle. The prior art fluorometer normally includes a high intensity steady state light source such as a one hundred fifty (150) watt tungsten halogen light and with this light filtered with a blue filter to give blue exciting light. The fluorescent light is collected by the remaining fibers in the group and is filtered by a yellow-green filter. The light energy passed by the yellow-green filter is directed to a photomultiplier so as to provide a measurement of the collected fluorescent light energy.

The above described type of prior art device is relatively large, expensive and is sensitive to ambient light. In particular, sensitivity to ambient light is so critical that the device usually includes a shield so as to prevent the entry of any ambient light into the device when making the measurement of fluorescense. As an alternative, the measurement may be made in a dark room but such a measurement in a dark room is obviously difficult to perform.

SUMMARY OF THE INVENTION

The present invention provides for an improved fluorometer for monitoring blood flow such as nutritive blood flow into body tissue. The fluorometer of the present invention is inexpensive, small and is not sensitive to ambient light. The fluorometer of the present invention uses a solid state detector instead of the prior art photo-multiplier and the use of the solid state detector reduces the cost of the device and eliminates the necessity of a high voltage power supply. One difficulty with the use of a solid state detector is that a solid state detector with its associated amplifier is much noiser electrically than a photomultiplier. The electrical noise would generally be overcome by using a large light source. However, in the present invention, the electrical noise is overcome by the use of phase sensitive detection to reduce the sensitivity to noise and as an additional advantage, the phase sensitive detection makes the device of the present invention insensitive to ambient light.

In order to provide for phase sensitive detection, the light source must be modulated, either by pulsing the light source or by using a mechanical chopper to interrupt the light beam. In order to maintain the small size of the device so that the device may be hand held, a mechanical chopper is not used and the present invention incorporates a pulsing of the light source. In the prior art it is generally considered best to use the largest light source possible so as to provide for the maximum amount of exciting light. However, a large light source necessitates a large filament and large filaments have large rise times which are counter productive to the proper pulsing of the light source. For example, as pulsed electrical energy is supplied to the light source, the filament is heated and because of the large rise time for large filaments, the filament would appear to have a steady state output rather than a pulsed light output. The proper pulsing of the light source is compounded by the fact that gas filled halogen bulbs have very slow decay times. It is preferable to use a halogen bulb because such a bulb allows for a high filament temperature to provide for sufficient light energy in the blue region.

In order to accomplish the pulsed light source and to overcome the various problems described above, the present invention provides for the use of a low wattage light source with a small filament and the use of such a light source is generally the reverse of what is provided for in the prior art. In particular, the size of the light source of the present invention is defined in accordance with the following criteria. In order to get reasonable noise rejection, the phase sensitive detection should provide for an integration of the detected flurosecent light over approximately ten (10) cycles of light energy from the light source. The instrument response time should not be too long and if a response time of one (1)

second is chosen, the light source is thereby pulsed at at least ten (10) Hz. If, for example, a two (2) watt bulb is chosen, then the pulsing of the bulb can occur between a range of between ten (10) to twenty (20) Hz. The light bulb need not go all the way off but there should be a sufficient flicker of at least fifty percent (50%) so as to provide for a proper pulsed light output.

If a larger light source is chosen there is no substantial gain in efficiency. Although a larger light source will provide for more output light energy, the larger rise and decay times of the larger bulb produce a smaller percent modulation. It has been determined that the modulated light output is about the same independent of the bulb size when the bulb size is larger than about six (6) watts. For example, the bulb size of the present invention would normally be limited to be at most twenty (20) watts which is slightly more than one-tenth (1/10) the power that is normally used in prior art fluorometers.

The use of the small wattage bulb for the fluorometer of the present invention also provides for three (3) additional advantages. First, a smaller wattage bulb means lower power consumption and thereby less heat to be dissipated. This is of considerable importance if the instrument is to be hand held. Second, the smaller wattage bulb is smaller in size and therefore allows for smaller packaging which is again important for a hand held instrument. Lastly, the smaller wattage bulb has a small filament and therefore it is easier to focus the light from the smaller filament to a small region which is desirable with the device of the present invention. Because of the use of the smaller filament it is possible to get more usable modulated light to the region of skin tissue of interest with the use of the small bulb than with a big bulb.

The present invention also is directed to a hand held flurometer which may use fiber optics to direct the modulated light to an area of interest for excitating and with the fluorescent light collected and carried by a light pipe or optical fibers to a solid state detector. The various electronics for the pulsing of the light source and performing the phase sensitive detection may be built into the handle of the hand held device. In addition, the measurement of the fluorescent level may be displayed on a visual readout which is also part of the hand held device.

Alternatively, the various electronics and display may be positioned within a shelf or table mounted cabinet and with the light brought to the area to be measured and collected from that area using long optical fibers in a bundle. Since the fibers themselves tend to fluoresce, the fibers carrying the blue light and the returning fluorescent light are not the same fibers and the present invention uses a split bundle of fibers, half for the blue exciting light and half for the collected fluorescent light.

With both the hand held and the fiber optic embodiments of the present invention, a light mixer is used to position the source of exciting light and the collection of fluorescent light to be at a distance above the skin tissue. This insures that the entire desired area of skin tissue is excited with light energy and with the fluorescense detected from the same area.

BRIEF DESCRIPTION OF THE DRAWINGS

A clearer understanding of the invention will be had in reference to the following descriptions and drawings wherein;

FIG. 3 illustrates a long tip accessory for the fluorometer of FIG. 1 for providing measurement at an internal position;

FIG. 4 illustrates an alternative structure for providing and collecting light energy for the hand held fluorometer of FIG. 1;

FIG. 5 illustrates a second embodiment of the invention including long fiber optics to bring the exciting light to and the returning light from the surface to be measured;

FIG. 6 illustrates the fiber optics of FIG. 5 within a monitoring system for permanently monitoring small surfaces areas; and FIGS. 7a and 7b illustrate an accessory item used to insure that the same surface area is monitored for successive measurements.

DESCRIPTION OF THE PREFERRED EMBODIMENTS

Figure 1:
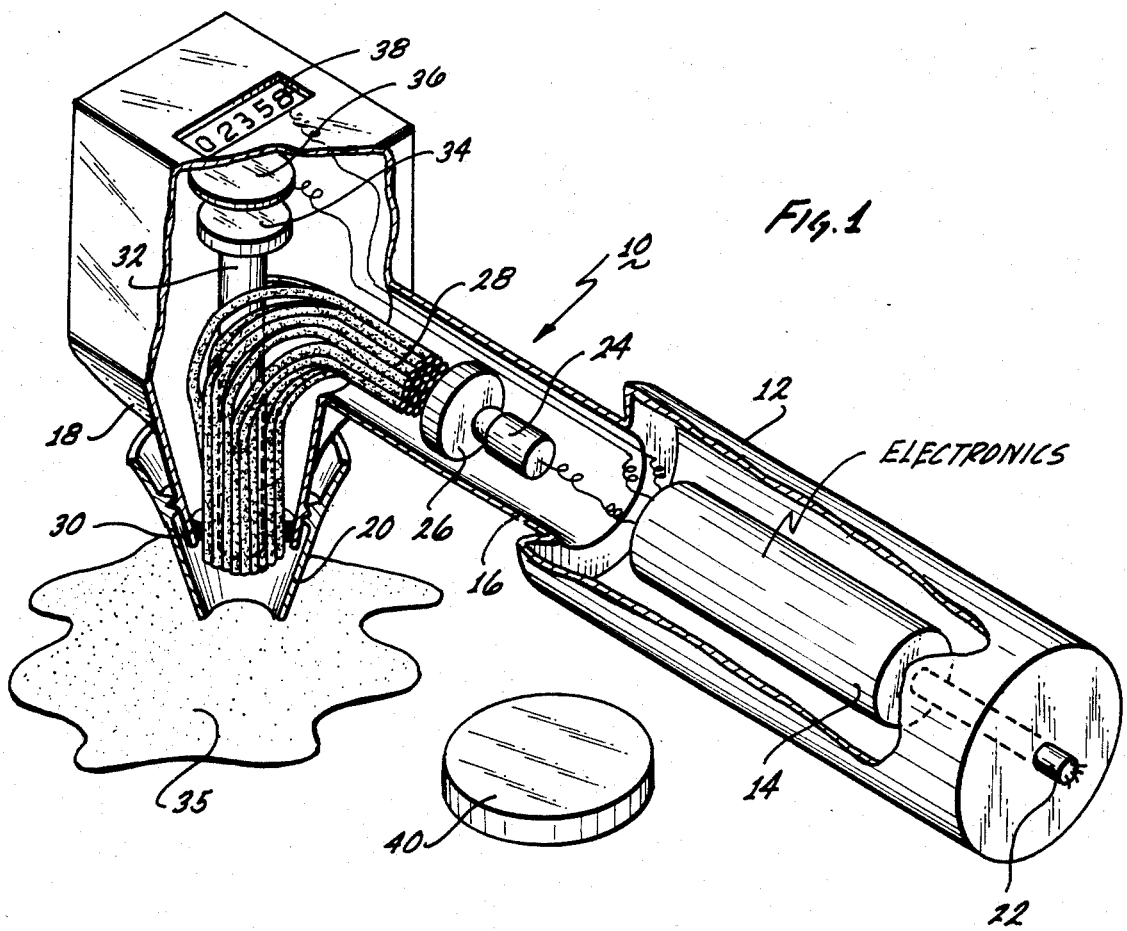
FIG. 1 illustrates a perspective view of a hand held skin fluorometer perfusion monitor.

FIG. 1 illustrates a perspective view of a hand held fluorometer 10 constructed in accordance with the teachings of the present invention. The hand held instrument 10 is essentially constructed in three (3) sections. A first handle section 12 is used to contain the various electronics 14 provided with the fluorometer 10. Extending from the handle 12 is an intermediate section 16 which is used to primarily contain the exciting light source. Finally, a head section 18 contains the fluorescent detection portion of the system and a visual display. A replaceable tip 20 may be positioned at the light emitting and detecting end of the head 18.

As indicated above, all of the various electronics 14 for the fluorometer may be contained in the handle portion 12. A power cord 22 supplies electrical power to the electronics and through the electronics to the other portions of the fluorometer of the present invention. In particular, pulsing electrical energy is supplied from the electronics 14 to a tungsten-halogen lamp 24 and with the halogen lamp providing a spectrum of light energy including significant light energy in the blue region. A blue filter 26 is positioned to pass essentially the blue exciting light from the light source 24 to the end of a fiber optic bundle 28. The blue exciting light is therefore passed through the fiber optic bundle 28 from the intermediate section 16 into the head section 18 and is guided to the end of the head section 18 to be emitted as blue emitting light at an end position 30 for the bundle. The bundle of fiber optics 28 is actually formed in a circular path to surround a solid light guide or pipe 32 so that the end emitting light portion 30 is formed as a cylinder. The light energy is then directed toward the skin surface 35 to impinge on an area of the skin surface defined by the opening in the replaceable tip 20.

The blue emitting light thereby excites any fluorescence in the skin 35, due, for example, to the injection of a fluorescent dye into the blood stream and with the fluorescent light returning to the instrument through the solid light guide 32. Normally, if a blue exciting light is used, the fluorescence will be in the yellow-green region and so at the end of the light guide 32 a yellow-green filter 34 is positioned to pass essentially only the light in the yellow-green region to a detector 36. Part of the output signal from the detector 36 represents the fluorescent energy and this energy is measured by the electronics 14 and with this measurement then provided by the electronics 14 to a digital readout 38 located at the back of the head section 18. It is to be appreciated that as an alternative to using power supplied through the cord 22, such as from a separate power supply, the handle may also be fitted with a battery pack, so that the entire unit may be completely self-contained and portable.

Figure 2:
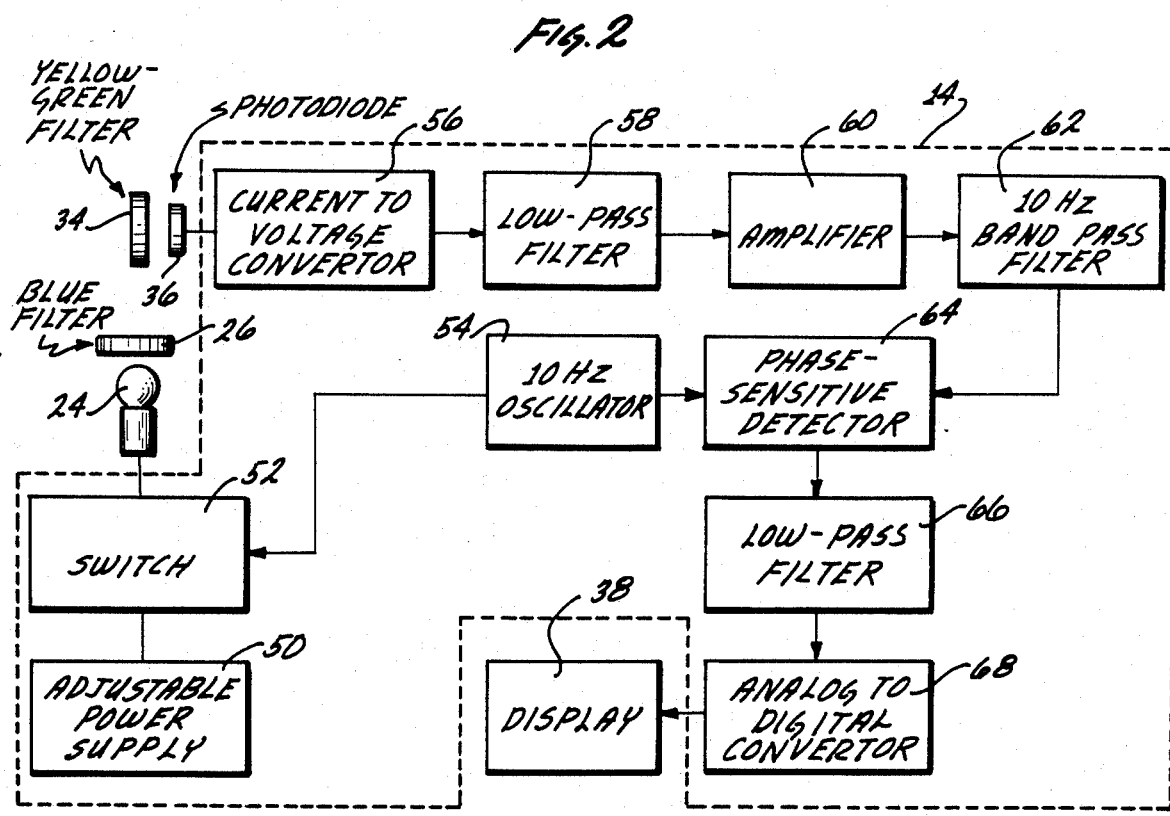
FIG. 2 is a block diagram of the various electrical components which form the circuit for the fluorometer of FIG. 1.

As shown in FIG. 2, the electronics 14 may include the following items as shown in the dotted portion. Power is supplied to the electronics 14, such as through the cable 22 shown in FIG. 1 or through the use of a portable power supply such as a battery pack mounted in the handle 12. The power supply supplys power to all of the components forming the electronics 14. In particular, an adjustable power supply 50 supplies power through a switch 52 to the halogen lamp 24. The switch 52 is controlled by a ten (10) Hz oscillator 54 so that the output from the lamp 24 is a pulsing output light at a ten (10) Hz rate.

The pulsing output light from the lamp 24 passes through the blue filter 26 and is directed to an area of the skin such as with the optical system shown in FIG. 1. The blue light causes the fluorescent dye in the skin to fluoresce to produce pulsing light energy in the yellow-green region representative of the fluorescence. The light energy in the yellow-green region including ambient light is passed through the yellow-green filter 34 to be received by the detector 36 which is preferably a solid state photo diode. The output from the photo diode is representative of the yellow-green light. The light energy is coupled to a current-to-voltage converter 56 to produce an output voltage representative of all the yellow-green light energy. This output voltage is then passed through a low pass filter 58 and with the signal from the low pass filter 58 then amplified by an amplifier 60.

The signal from the amplifier 60 is then passed through a ten (10) Hz band pass filter 62 and with both the signal from the filter 62 and the signal from the oscillator 54, coupled to a phase sensitive detector 64. The detector 64 provides for an output signal representative of the pulsing yellow-green light energy pulsing in phase with the light source and this output signal is passed through a low pass filter 66 and then is converted to a digital signal by a digital-to-analog converter 68. The digital output from the digital-to-analog converter 68 is then displayed as a numerical readout representative of the fluorescent energy by the display 38.

The electronic system, as shown in FIG. 2, provides for an accurate reading of the fluorescent energy produced at the skin surface and with this reading not sensitive to ambient light. In particular, the detector 36, such as the solid state photo diode, sees in general three (3) sources of light. First, the solid state photo diode detects the fluorescent light from the tissue and with this fluorescent light pulsing at the same rate and in phase with the exciting light from the lamp 24. Second, the photo diode 36 sees light from any fluorescent room lights which would be pulsing at one hundred and twenty (120) times per second. Third, the photo diode sees light from incandescent room lights and/or sunlight, both of which form essentially a steady background light. In order to make an accurate measurement of the tissue fluorescence, without having to darken the room, it is necessary to eliminate the light from the second and third sources.

In the electronic circuit 14, the first stage after the detector 36 is the current to voltage converter 56 and the low pass filter 58. This first stage passes the signals from all three sources but converts a high percentage, such as ninety percent (90%), of the signal from the second source into a DC level. The next stage of the electronic circuit is the amplifier 60 and the band pass filter 62. This stage passes most of the signal from the first source but removes most of the DC level which thereby eliminates most of the signal from the second and third sources. However, since the ambient light can be quite strong, the remaining background signal may still be larger than the signal from the first source, which is the fluorescent light from the tissue.

The signal passed by the first and second stages of the electronic circuit 14, which consists of the pulsing fluorescent signal and whatever background signal is left is then coupled to the phase sensitive detector 64. The detector 64 passes essentially only the pulsing fluorescent signal since the phase sensitive detector compares the signal passed from the first and second stages with the output from the ten (10) Hz oscillator 54 and passes only the signal which is in phase with the signal from the oscillator 54. The low pass filter 66 averages the output from the phase sensitive detector 64 over a time equal to the time constant of the low pass filter. Therefore, a signal in phase and at the same frequency as the oscillator 54, such as the fluorescent signal from the tissue gives a non zero value when passed through the low pass filter, whereby signals such as a DC level or oscillating but not in phase with the oscillator, gives a signal which, when averaged over a period of time is zero.

In order to provide for a reasonable rejection of the background signal, the low pass filter should average over several pulses of the light source. However, it is desirable that the instrument provide for a reading within a reasonable time response, so that the operator may measure several areas of the skin in a short period of time. In general, it is desirable that the instrument provide for a measurement within a one (1) second time period. Because of this, the time constant of the low pass filter at the output of the phase sensitive detector 64 should be about one (1) second. In order to provide for good background suppression, it is desirable to average the signal over at least ten (10) pulses of the light source, thereby requiring a light that can be pulsed at ten (10) Hz or faster. This may only be accomplished if the bulb is quite small so that its filament is small and therefore its rise time is fast. In the present invention the preferred embodiment uses a two (2) watt bulb and in general the bulb should not be greater that approximately twenty (20) watts which is approximately 1/10th of the size of the bulbs normally used with fluorometers.

It is desirable to calibrate the fluorometer, so that the output reading at the digital display 38 is compared to an absolute scale. This is particularly true since the output from bulb to bulb can vary, the bulb can lose intensity with age and since the optics may get dirty from handling. It would be best to provide for a method of calibration which could be accomplished before each measurement so as to provide for an accurate comparison between different readings. In the prior art, instruments have been calibrated by using a calibration solution of fluorescein in water. This type of calibration is not satisfactory since fluorescein in water is not stable for long periods so that the calibration solutions need to be periodically renewed. Secondly, the solution may adhere to the measurement probe which can cause a background fluorescence independent of the fluorescence from the skin tissue. Lastly, the use of a water solution is messy.

In the present invention, the calibration is provided by a solid calibrator 40 shown in FIG. 1 formed from a plastic in which a fluorescent material is added during manufacture. This material is available from Rohm in Germany. The tip 20 of the fluorometer is placed on the calibrator 40 just as it would be on the skin and the adjustable power supply 50 is varied until the readout at the display 38 gives the proper level. This level may be represented by an arbitrary number such as 100 on the display. If desired, the calibration level may be cross-calibrated in terms of a certain concentration of fluorescein in water so that the output measurement is representative of an actual concentration of fluorescein as opposed to just an arbitrary measurement level which may be repeated from measurement to measurement.

There may be times when it is necessary to provide for a measurement either through a thick cast or on an internal organ such as during surgery and it is therefore desirable to provide for a long tip for the fluorometer of FIG. 1. This may be accomplished by mounting a solid light guide of an appropriate length in the removable tip 20 as shown in FIG. 3. In particular, a solid light guide 70 may be mounted in the tip 20 so as to be adjacent the end portion 30 of the fibers 28 and also adjacent the end of the light guide 32. The solid light guide 70 would carry both the blue exciting light and the collected fluorescent light and should be large enough to cover the ring of fibers 28 emitting the blue light at the end position 30 and also the light guide 32.

When the light guide 70, forming an extension, is used, the instrument would be recalibrated, for example, through the use of the solid calibrator 40. The measurement would then be made by pressing the end of the light guide 70 against the surface 35 which is to be measured. In the embodiment of the invention shown in FIG. 1, it is important that the end portion 30 of the fibers 28 and the light pipe 32 be spaced away from the surface 35 to be measured. This spacing may either be provided by air, as shown through the use of the removable tip 20 or could be provided by a solid light guide such as the light guide 70 shown in FIG. 3 or a shorter light guide similar to that shown by the light guide 70. In either case, the light guide would be of a size to cover both the fibers 28 carrying the blue light and the light guide 32 which collects the fluorescent light. The air space or light guide forms a mixer since this area mixes up the outgoing blue light and the returning yellow light in this space.

The reason for the use of the air space or light guide forming the mixer is to insure that the end of the light guide 32 which collects the fluorescent light views the same area which has been excited by the blue light. This provides for the maximum efficiency in the collection of the fluorescent light. If the end portion 30 of the fibers 28 and the end of the light guide 32 were placed directly on the skin 35 with no space, the blue light would excite one area of the skin and the light pipe 32 would view another area and would thereby see little fluorescent light. With the use of the mixer, the blue light is directed to a particular area and the fluorescent light is collected from the same area by the light pipe 32 thereby providing for a high efficiency in excitation and collection.

If an air space is used to form the mixer, then the distance for the spacing should be approximately of a size equal to the radius of the light pipe 32. For example, measurements have been made of the amount of collected fluorescent light versus the distance the light pipe 32 is from the surface being measured. For a light pipe having a diameter of one-fourth inch ($\frac{1}{4}$"), the amount of collected light peaks when the light pipe is approximately one-eighth inch ($\frac{1}{8}$") from the surface being measured. If a light pipe, such as the light pipe 70, is used to provide for a mixer, then the minimum length for this light pipe should be also about equal to the radius of the collecting light pipe 32. However, once the minimum length is provided any greater length may be arbitrarily long since once the exciting and collecting light is mixed the light pipe maintains this light energy within the confined volume of the light pipe 70 and a greater length does not result in any appreciable loss of light energy.

As as alternative to the use of the fiber optic and light pipe system shown in FIG. 1, the head section 18 of the hand held instrument may contain a lens systems as shown in FIG. 4. In particular, a light source 20 such as a tungsten-halogen lamp may direct light energy through a focusing lens 82 and through a blue filter 84 to be focused in an area 86 at the surface of the tissue 35. Returning fluorescent energy would be passed through a lens 88 and a yellow-green filter 90 to be focused on a photo diode 92. The remaining portion of the electronic system would be as shown in FIG. 2. The light source 80 would be of low wattage, such as a two (2) watt bulb, and with the light source pulsed and detected as shown in FIG. 2.

One other preferred aspect of the present invention is in the use of a particular type of solid state detector or photo diode. Specifically, a gallium arsenide phosphide (GaAsP) detector is preferred rather than a silicon photo diode, although silicon is generally considered preferable for use as a detector. The reason the GaAsP detector is preferred is that this type of detector is not sensitive to wavelengths longer than seven hundred (700) nm and therefore any infra-red light which passes through the filter is not detected.

As a second embodiment of the invention, the light energy may be brought to the surface to be measured and then collected using long optical fibers. The electronics 14, the light source and detector are positioned at a remote station and with the long fiber optic system providing for the excitation and collection. Since the optical fibers themselves tend to fluoresce the fibers carrying the blue light and the returning fluorescent light should not be the same fibers. This may be accomplished using a split bundle of optical fibers, half for the blue light and half for the fluorescent light as shown in FIG. 5.

As shown in FIG. 5, the blue light is transmitted to a first half 100 of a split optical fiber bundle and the fluorescent light is collected by a second half 102 of the split bundle. The entire bundle is shown joined at the position 104. If the fibers in the two halves 100 and 102 are randomly mixed in the portion 104, then it would be possible to position an end 106 of the bundle 104 adjacent the tissue 35. However, a mixer 108, which is formed as a solid light pipe, may be used so as to eliminate the necessity of providing for a randomly mixed bundle. When the mixer 108 is used, all of the emitting fibers 100 can be on one side of the bundle in the portion 104 and all of the collecting fibers 102 can be on the other side. The mixer 108 insures that at the surface 35 to be measured, the emitting and collecting fibers both view the same area.

Since the mixer 108 is relatively short it does not provide any appreciable fluorescence of its own. If all of the emitting fibers are on one side and all of the collecting fibers are on the other side, then the length of the mixer should be approximately the radius of the bundle 104. If the emitting and collecting fibers are randomly mixed within the portion 104, it is still possible to increase the efficiency through the use of a mixer but in this case, the mixer can be quite short, such as the radius of one of the fibers in the bundle 104.

The fiber optic embodiment of the invention, as shown in FIG. 5, may be particularly useful for continuous monitoring, since the end of the fiber optic bundle may be attached to an area of the skin to be continuously monitored and can be easily taped in position similar to the taping of tubing now provided for in the hospital.

The continuous monitoring provided for by the embodiment of FIG. 5, allows for the measurement of local skin blood flow per unit volume by injecting fluorescein in very small quantities into the dermis and monitoring the washout of the fluorescein due to the blood flow carrying it away. The quantities for example, may be one (1) microgram of fluorescein diluted into a volume of water. With this method it is possible to measure the blood flow per unit volume for the tissue. In general, as with all single injection indicator dilution, the concentration of the indicator decreases exponentially where:

$$C(t) = C(o)e^{-t/\tau} = \text{Concentration of fluoroscein}$$

where
$\tau = \text{Volume/Flow}$
so that flow/unit volume $= 1/\tau$

For good flow $\tau$ is about five (5) minutes, i.e., the flow/unit volume is about 0.2 ml/sec.cc. This assumes that the fluorescein in the tissue can diffuse freely into the blood vessels. This is true for fluorescein since it does not attach to the tissue.

The standard way of using fluorescein is to measure tissue perfusion by the injection of approximately one hundred (100) mg of fluorescein to the central blood system and with a subsequent measurement of the appearance of the fluorescein in the tissue. For a newly transplanted piece of skin, for example, this provides a measure of the blood flow into the skin (arterial flow) but it would also be desirable to know if there is venous flow out of the tissue. It is important to know that the venous flow is not occluded since if the venous flow is occluded, this could be corrected by surgery. By using the local injection technique described above, a subsequent measurement may be made of the washout of fluorescein. This provides for a direct indication of the venous flow out of the tissue. If the venous flow is occluded the washout is very slow. The amount of injected fluorescein is very small, such as 1/100,000 times the normal injection, and this method may be used not only to monitor washout but also may be used for the patients who become nauseous from the use of large amounts of fluorescein.

In order to monitor the washout, the structure shown in FIG. 5 is used and with the end of the fibers taped to the tissue or attached with a holder. A relatively small bundle of fibers is used and the device is constructed to collect data, store that data and provide an output display of the flow/volume. The use of the small pulsing light source and the phase sensitive detection, as shown in FIG. 2, provides for the detection of the fluoroscense. The resultant monitor therefore combines the fiber optic structure, as shown in FIG. 5, with the small pulsing bulb and phase sensitive detection, as shown in FIG. 2, to produce the resultant system shown in FIG. 6.

In the system of FIG. 6, the output from the electronics 14 is coupled to a computer 110. The computer collects the data, stores the collected data and then produces a fit of an exponential curve to the data to determine flow/unit volume. The output flow/unit volume may then be displayed by a display 112.

With both embodiments of the invention, it is important to provide for a reproduction of measurements of the skin tissue at the same area so as to produce an accurate time sequence of measurements from the same area. This may be particularly important when using the washout technique as described above. The present invention therefore includes an accessory to insure that the measurement is made on the skin at the same area each time. Specifically, the present invention incorporates the use of donut shaped patches in which the center hole is the same size as the tip of the fluorometer and with these patches pasted on the skin in the desired location. With the use of an individual patch or a series or patches on the skin, measurements can be repeated at the same spot or spots by simply placing the tip of the fluorometer in the center of the donut.

Two (2) alternative donut structures are shown in FIGS. 7a and 7b. In FIG. 7a a round donut 120 has a center opening 122 which is the same size as the tip of the fluorometer. The donut may be adhesively attached to the tissue 35 so that the measurement is at the same position on the skin each time. This has been found to be important since changing the position of the reading on the skin even a small amount, can affect the magnitude of the reading.

As shown in FIG. 7b, the patch may have a different shape such as the rectangular patch 124 of FIG. 7b. This rectangular patch 124 is larger than the patch shown in FIG. 7a. This allows for indicia to be applied to the patch so as to identify the particular patch. Patch 124 also has an opening 126 to insure that the measurement is made at the same position each time. In addition, the patch 124 may include a transparent layer 128 so that the tip of the fluorometer does not contact the skin during measurement.

The present invention therefore is directed to skin perfusion fluorometry and in particular, to the use of a fluorometer which incorporates an exciting light source of a small wattage, such as less than twenty (20) watts, which can be pulsed at a frequency of at least ten (10) Hz. The detection of the fluorescent light is accomplished using phase sensitive detection so as to decrease electronic noise and make the fluorometer impervious to ambient light. The exciting and collected light from the tip of the fluorometer is mixed so as to increase the efficiency of the collected fluorescent light. In general the length of the mixer is at least as large as the radius of the fiber optic bundle or collecting light pipe. The present invention may provide for the measurement of local wash out flow using a fluorescent dye dilution technique and with a continuous monitoring of the fluorescense over a period of time. In order to insure that the measurement is provided at the same place on the skin, the present invention also includes the use of patches to position the measurement at the same point for repeated measurements.

Although the invention has been described with reference to particular embodiments, it is to be appreciated that various adaptations and modifications may be made and the invention is only to be limited by the appended claims.

I claim:

1. A method of measuring local blood flow in skin tissue using fluorescent dye dilution, including the following steps:

injecting a fluorescent dye solution into the blood stream, producing light energy from a light source including light energy at first particular frequencies and with the light sources having a wattage rating of no more than twenty (20) watts, pulsing the light energy, filtering the pulsing light energy from the light source to pass substantially only the light energy at the first particular frequencies, directing the filtered pulsing light energy to a portion of the skin tissue containing fluorescent material, collecting light energy including fluorescent light energy at second particular frequencies produced at the portion of the local area and directing the collected light energy away from the skin tissue, filtering the collected light energy to pass substantially only the collected light energy at the second particular frequencies, producing a first signal in accordance with the filtered collected light energy, producing a second signal in accordance with the first signal and representative of the filtered collected light energy in phase with the filtered pulsing light energy which second signal is representative of the fluorescent light energy at the second particular frequencies produced at the portion of the skin tissue, and using the magnitude of the second signal as a measure of the relative blood perfusion in the skin tissue.

2. The method of claim 1 wherein the step of pulsing the light energy provides pulsing at a frequency of approximately ten (10) Hz.

* * * * *